(12) United States Patent
Goldenberg

(10) Patent No.: US 7,621,923 B2
(45) Date of Patent: Nov. 24, 2009

(54) SNARE COIL RETRIEVAL DEVICE FOR CAPTURING AND RETRIEVING A SPECIMEN

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 250 days.

(21) Appl. No.: 11/678,478

(22) Filed: Feb. 23, 2007

(65) Prior Publication Data

US 2008/0208075 A1 Aug. 28, 2008

(51) Int. Cl.
*A61B 17/22* (2006.01)
(52) U.S. Cl. .................... 606/127; 604/267; 606/159
(58) Field of Classification Search ............. 606/127, 606/128, 200, 170, 194, 110, 113, 114, 167; 604/159, 22, 267
See application file for complete search history.

(56) References Cited

U.S. PATENT DOCUMENTS 5,849,011 A * 12/1998 Jones et al. ............. 606/47
6,428,551 B1 * 8/2002 Hall et al. ............... 606/159
6,589,230 B2 * 7/2003 Gia et al. ................. 606/1
6,855,155 B2 * 2/2005 Denardo et al. ......... 606/200
2002/0193735 A1 * 12/2002 Stiger ................. 604/101.01
2003/0181876 A1 * 9/2003 Ahn et al. ............... 604/267
2004/0249337 A1 * 12/2004 DiFiore .................. 604/40
2005/0054948 A1 * 3/2005 Goldenberg ............ 600/567
2005/0283166 A1 * 12/2005 Greenhalgh ............ 606/113

* cited by examiner

*Primary Examiner*—Anhtuan T Nguyen
*Assistant Examiner*—Jocelin C Tanner
(74) *Attorney, Agent, or Firm*—Leason Ellis LLP

(57) ABSTRACT

A retrieval device for retrieving and capturing a foreign body specimen, such as a tissue specimen or a foreign material specimen, according to one exemplary embodiment includes an outer cannula member having an inner lumen and an inner member received within the inner lumen such that the inner member can rotate relative to the outer cannula. The inner member has a distal end that extends beyond a distal end of the outer cannula. The device also includes a first snare coil having a first end and an opposing second end. The first end of the snare coil is attached to an outer surface of the outer cannula and the second end of the snare coil is attached to the inner member to allow the snare coil to be actuated by rotating the inner member relative to the outer cannula so as to either open or close the snare coil for collecting the specimen.

18 Claims, 5 Drawing Sheets

SNARE COIL RETRIEVAL DEVICE FOR CAPTURING AND RETRIEVING A SPECIMEN

TECHNICAL FIELD

The present invention relates to a surgical instrument, typically known as a retrieval device for retrieving a target specimen and more particularly, relates to a minimally invasive retrieval device that allows an operator to more precisely manipulate the retrieval mechanism for efficient engagement with a foreign body resulting in improved retrieval rates of foreign body materials that are located in certain vascular or nonvascular spaces.

BACKGROUND

Patients are undergoing more intravascular and minimally invasive procedures as alternatives to open surgical procedures. These less invasive procedures use a variety of catheters, and other devices which are placed in vascular, abdominal, pulmonary, urologic spaces with the goal of manipulating, cutting, and stabilizing structures at a distance from the operator. As every procedure has a certain failure rate, there will be by definition cases or instances where a component of the device separates and is difficult to retrieve or a material is placed or separates from a device and needs to be captured and removed.

In the setting of vascular procedures, a catheter segment, wire or balloon segment may become dislodged and must be recovered. In the setting of minimally invasive surgical procedures, a device component, suture clip, or staple, may be lodged in a small cavity or region where retrieval might be compromised or difficult with typical minimally invasive surgical devices. In the practice of biliary endoscopy and urology, stents and other catheters or other dislodged components may require subsequent retrieval.

Standard or direct explorations or excisions of the device elements or retained materials, can be overly invasive and traumatic, and inconsistent with the basic principles of minimizing direct trauma through minimally invasive procedures. Therefore, minimally invasive devices and techniques have been developed to retrieve dislodged foreign objects from the body.

Moreover certain pathologic materials, such as thrombi, emboli or stone excrescences, can be difficult to capture within delicate small spaces and require devices that can easily and efficiently capture or grab them for retrieval.

The use of retrieval devices for the removal of stones within the ureters, or bladder or within the biliary system are examples of the application of retrieval devices to remove pathologic materials that previously required open procedures, which often were associated with significant morbidities.

The development of stones within the ureters can result in renal insufficiency and recurrent infections. Removal of the stones can reverse obstructive phenomena, decrease pain, improve renal function and decrease recurrent infections. Biliary stones dislodged from the gallbladder can result in recurrent biliary obstruction, jaundice, pain and infection which can be alleviated by removal of the obstructing stone elements.

The development of a thrombus or dislodgment of an embolus within a vascular space results in downstream ischemia which can have profound physiologic consequences. If such an event occurs within the central nervous system, focal brain ischemia ensues resulting in the clinical manifestations of a stroke. The development of a thrombus or the dislodgment of an embolus into the peripheral vasculature can result in limb ischemia. Thrombi that develop in the coronary arteries result in myocardial infarctions.

Retrieval devices have been developed and applied to recovering vascular thrombi or emboli. The procedure of removing such a thrombosis is called an embolectomy and has been used by Interventional Radiologists and Vascular surgeons therapeutically. Removing these thrombi or emboli with minimally invasive procedures can be efficient and potentially less morbid then open direct procedures.

A number of retrieval devices have been designed and have entered the commercial marketplace. While a number of devices exist in the industry, there are generally four distinct type of devices that have gained more widespread popularity and use. In particular, the four types of devices can be referred to and identified as the (1) Gooseneck design snare; (2) Texan snare; (3) En Snare; and (4) the In Time retrieval device.

A review of some of the more common prior art devices reveals that the devices can be divided into three types of designs. The first type of design is a single snare or multiple looped snares that project from a catheter where the diameter of the snare loop or loops is controlled by advancing or retracting the catheter "over" the looped wire system or alternatively by advancing or retracting the wire system within a relatively stationary catheter system. The wire loop or loops can be manipulated or stabilized by the operator by a long wire which is connected to the loop or snare and extends distally to the proximal portion of a catheter system. Examples of this type of system include the Amplatz gooseneck system or the En Snare system marketed by InterV.

The second type of design is that of a mesh or basket configuration defined by multiple loops or struts that can be deployed through a catheter system. The basket or mesh system is attached to a wire which extends through a catheter system and is available to the operator at the proximal portion of the catheter. The geometry and therefore activation of a mesh system is controlled by the relative positions of the catheter meshed/wired structure. In some sense the relationship and control of the geometry of the wire loops is similar to a device of the first type in that a catheter initially constrains and keeps the wire mesh system from expanding as it is retained within the catheter lumen. Once the basket or mesh system is advanced through the catheter, it may expand to its fully deployed geometry.

After engaging a foreign body, the basket or mesh system can be retrieved by uniformly pulling back on the wire and catheter without changing the longitudinal relationship of the two components, hopefully with the foreign body engaged. Alternatively, the deployment catheter can be pushed back over the mesh system partially to change the geometry of the system and produce a capturing force along the surface of the foreign body. After such a maneuver, the longitudinal relationship of the activated mesh system and catheter are maintained and the system is removed hopefully with the foreign body.

A third type of device incorporates a multi-wired basket-like structure located at the end of a catheter system. The In Time retrieval system marketed by Boston Scientific is an example of this type of system. A wire mesh or multi-strutted system is attached to the tip of a microcatheter. The mesh or basket element appears not to be designed to be deployed from within the catheter system but is attached to its most distal end. The geometry of the mesh capturing system is controlled by a core wire that passes through the catheter system and attaches to the distal aspect of the mesh or basket system. The capturing element is "opened up" that is the spaces between the wires or struts are increased by decreasing the longitudinal length of the basket system by pulling back with the core wire. Once a foreign body is engaged within the capturing mesh wire system the spaces between the capturing struts can be decreased by elongating the wire system by advancing the core wire forward or distally. There is a possibility that the mesh system can be rotated by rotating the core wire. More specifically, the In Time product is made of a Nitinol braided microcatheter shaft, a radiopaque retrieval basket and a steerable Nitinol core wire.

There are a number of shortcomings in the design of the above-described conventional devices and their application in clinical practice which limit their effectiveness and/or simplicity.

The success of the retrieval procedure depends on the ability of the retrieval device to efficiently and reliably capture the foreign material. The initial steps of the procedure require that the retrieval device must come in contact with the foreign material in a way that allows the device to engage it or grab it. The efficiency of that step depends on the ability of the operator to control the position and contour of the wires/mesh in relation to the foreign material. Based on the design of the devices of the first type of retrieval devices, it may not be easy to change the contour or geometry of the snare loop by manipulating a wire at the proximal end of the catheter system. Rotating the catheter or the internal wire by rotating the wire at the proximal end of the catheter may not translate efficiently into controllable movements of the snare loop that will facilitate precise localization of the loop adjacent to the foreign material.

With respect to devices that are either of the second or third types in which the capturing element is a mesh or basket-like configuration, individual control of any particular wire loop within the mesh may be more problematic. The design concept in this type of system focuses on the fact that when deployed, the mesh system provides multiple "openings" through which a material potentially will be engaged. However, the fact that there is an increased number of notches or gaps in which a foreign material may enter only increases the probability that such an event will occur and does not guarantee it. The engagement is a relatively chance event and not necessarily driven by a precise alignment and control of a wire loop in the region of the foreign material. Also some of these designs depend on converting longitudinal translation of the core wire relative to the microcatheter into the precise localization of a wire or multiple wires which can be technically cumbersome.

The ability to engage a foreign material and capture it within the central portion of the basket structure can be compromised by the complicated woven structure of the basket wires which may impede transit and positioning of the foreign material within the basket's central portion.

The ability of the foreign material to remain securely engaged with the retrieval device depends not only on the force to which the material is exposed but the surface area of the grabbing or engaging element which is in contact with the foreign material.

The first type of device generally has one or a few snare loops that engage the foreign material. When the loop size is decreased, the foreign material is pushed against either the tip or distal side of the catheter. Although bringing the foreign material adjacent to the side of the catheter increases the surface area for contact, this type of orientation usually only applies to devices with a single capturing loop and the precision and geometry of engagement may not maximize surface area contact.

The surface area of engagement in devices that are either of the second or third types is limited to the surface area described by one or multiple relatively small diameter wires. If a foreign material is engaged between two wires, there will be minimal surface area in contact with the foreign material compromising the reliability of the capture. Of course, if the foreign material finds its way into multiple notches or gaps, the total contact surface area will increase and the engagement will be more secure. However the second possibility may only occur by chance since as above it is difficult to precisely direct such a mesh element to engage with a foreign material at multiple sites.

Although these types of devices can be useful in certain applications, other devices that maximize their ability to precisely, efficiently and securely capture foreign and pathologic objects may be more useful to the interventionalist.

The object of the present invention is to provide a device that overcomes these deficiencies and improves the retrieval procedure.

Other features and advantages of the present invention will be apparent from the following detailed description when read in conjunction with the accompanying drawings.

SUMMARY

A retrieval device for capturing and retrieving a target specimen, such as a foreign body material, that is located in certain vascular or nonvascular spaces according to one exemplary embodiment includes an outer cannula member having an inner lumen and an inner member received within the inner lumen such that it can rotate relative to the outer cannula. The inner member has a distal end that extends beyond a distal end of the outer cannula. The device also includes a first snare coil having a first end and an opposing second end. The first end of the snare coil is attached to an outer surface of the outer cannula and the second end of the snare coil is attached to the inner member to allow the snare coil to be actuated by rotating the inner member relative to the outer cannula so as to either open or close the snare coil for collecting the foreign body material (which can be a tissue specimen or other material, such as hardened foreign material, etc.).

In another embodiment, the retrieval device includes at least a second snare coil having a first end and an opposing second end. The first end of the second snare coil is attached to the outer surface of the outer cannula and the second end of the second snare coil is attached to the inner member to allow the second snare coil to be actuated by rotating the inner member relative to the outer cannula so as to either open or close the snare coil for collecting the tissue specimen. The first and second snare coils can be interleaved with one another. When two or more snare coil wires are used, they can be arranged to form a mesh-like structure.

In another embodiment, the inner member is in the form of an elongated inner cannula having a proximal end and a distal end and an inner lumen formed therein. The device further includes an expandable member (e.g., a balloon) that is disposed at the distal end of the inner cannula and a connector member disposed adjacent the expandable member. The second end of the snare coil is attached to the connector member.

The device can also be constructed so that during actuation of the snare coil, the snare coil opens in an uneven manner as measured by the diameters of the loops of the snare coil as it is opened. For example, a proximalmost loop of the snare coil can have a greater diameter compared to the other snare coil loops as the snare coil is opened.

The snare coil can be formed of a material that has memory so that the snare coil has a predetermined, defined geometry as it opens. For example, the predetermined, defined geometry is one in which a coil diameter is greater in a proximal region of the snare coil compared to a distal region of the snare coil as measured when the snare coil is in an open position.

A retrieval device for capturing and retrieving a target specimen, such as foreign body material, that is located in certain vascular or nonvascular spaces according to yet another embodiment includes an outer cannula member having an inner lumen and an inner member received within the inner lumen such that the inner member can rotate relative to the outer cannula and optionally, also can move longitudinally within the inner lumen. The inner member has a guide channel formed therein, with the guide channel being open at the distal end and an opposite proximal end. The retrieval device includes a first snare coil having a first end and an opposing second end. The first end of the snare coil is attached to an outer surface of the outer cannula. The snare coil has a portion that is looped about the outer cannula from the first end of the snare coil to the opening of the guide channel at the distal end where the snare coil enters the guide channel and extends therethrough such that the second end of the snare coil passes through the opening of the guide channel at the proximal end of the inner member to allow a length of the snare coil to be varied by an operator for increasing a diameter of the snare coil loops. The snare coil is actuated by rotating the inner member relative to the outer cannula so as to either open or close the snare coil for collecting the foreign material (specimen).

In yet another embodiment, a retrieval device for capturing and retrieving a target object, such as foreign body material, that is located in certain vascular or nonvascular spaces includes an outer cannula member having an inner lumen and an inner member received within the inner lumen such that the inner member can rotate relative to the outer cannula. The device includes a first snare coil having a first end and an opposing second end. The first end of the snare coil is attached to an outer surface of the outer cannula and the second end of the snare coil is attached to the inner member to allow the snare coil to be actuated by rotating the inner member relative to the outer cannula so as to either open or close the snare coil for collecting the tissue specimen.

According to the present invention, the second end of the snare coil can be configured or looped in a certain fashion so that it continues as a wire through the lumen of the outer cannula, and the wire can be simply rotated so that the rotation is translated into rotation of the snare coil around the outer surface of the outer cannula.

A handle assembly may be provided as part of the device and includes a movable handle. The handle is coupled to the inner member such that movement of the handle is translated into rotation of the inner member within the outer cannula to cause actuation of the snare coil.

BRIEF DESCRIPTION OF THE DRAWING FIGURES

The foregoing and other features of the present invention will be more readily apparent from the following detailed description and drawings figures of illustrative embodiments of the invention in which.

DETAILED DESCRIPTION OF PREFERRED EMBODIMENTS

Figure 1:
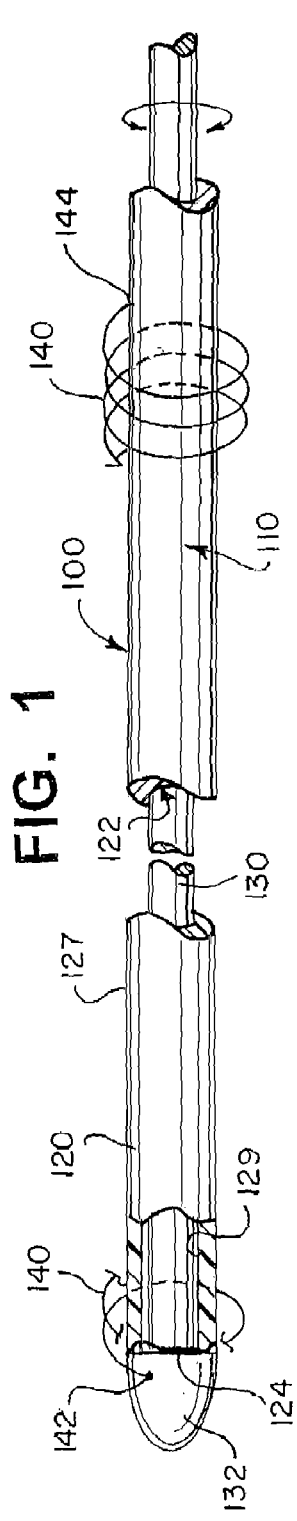
FIG. 1 is a side elevation view, in cross-section, of a specimen retrieval device according to a first embodiment.

Now referring to FIG. 1 in which a retrieval device 100 (specimen retrieving and capturing device) of a snare coil design is illustrated and is configured to retrieve a target specimen which can be in the form of a tissue specimen or a foreign material that is located in certain vascular or nonvascular spaces. To facilitate entry of the retrieval/capturing device 100 into vascular and nonvascular spaces or duct channels, the device 100 incorporates a catheter system 110. The catheter system 110 includes an outer catheter (outer cannula) 120 within which an inner member 130 is disposed and in particular, the inner member 130 can be in the form of a tube/catheter or a solid wire or rod. Both of these inner members 130, as well as others, are elongated structures that are shaped and dimensioned to be received within an interior (lumen) 122 of the outer catheter 120. The outer catheter 120 is typically in the form of an elongated tube that has an open distal end 124 and an opposite proximal end that is also an open end. The outer catheter 120 is a hollow structure with the interior 122 being in the form of an elongated bore or through channel formed the length of the outer catheter 120. The outer catheter 120 has an outer surface 127 and an opposite inner surface 129 that defines the bore 122.

The inner element 130 is designed and is positioned within the bore 122 so that it can be rotated within the outer catheter 120. The inner element 130 has an elongated structure and is defined by a distal end 132 and an opposing proximal end. The distal end 132 includes an area of increased dimension and in particular, the distal end 132 can have a head or a structure that defines a pointed end. In the illustrated embodiment, the head at the distal end 132 has a width that is greater than a diameter of the bore 122 and therefore, the head is prevented from entering the bore 122. The head at the distal end 132 thus acts as a stop that limits the longitudinal movement of the inner element 130 relative to the outer catheter 120. While the illustrated head has a rounded arcuate shape, the head can have any number of other shapes. However, it will be appreciated that the head does not have to act as a stop but instead can have dimensions less than the bore of the outer cannula 120 and therefore, the head will be received into the bore of the outer cannula 120.

The distalmost aspect (head 132) of the inner element 130 is thus an element that can rotate and attaches to a snare coil capturing component (snare coil) 140. The snare coil 140 has a distal end 142 that is attached to the head 132 using any number of different techniques and an opposite proximal end 144 that is connected to the outer surface 127 of the outer cannula 120. The proximal end 144 of the snare coil 140 is not attached at the most distal region of the outer cannula 120 but instead, the proximal end 144 is connected to the outer cannula 120 at a location that is spaced from the distal end 124 of the outer cannula 120. In contrast, the distal end 142 of the snare coil 140 is attached to the distal rotating end 132 of the inner element 130 (inner tube catheter). The remaining portion of the snare coil 140 surrounds the outer cannula 120.

Rotating the inner element 130 relative to the outer cannula 120 results in uncoiling the snare coil 140 with separation of the snare coil 140 from the outer cannula 120 and the inner element 130 (inner tube catheter) producing a space between the structures for capturing, namely, the snare coil 140 and the outer catheter 120. Re-rotating the inner element 130 relative to the outer cannula 120 in an opposite direction results in coiling the snare coil 140 back into its undeployed position and decreasing the space between the snare coil 140 and the outer catheter 120. If a foreign body is positioned between the outer catheter 120 and the snare coil 140, rewinding the snare coil 140 will cause the object to be compressed between the outer surface of the outer cannula 120 and the inner surface of the snare coil 140 thus capturing or securing it for removal.

Many variables, such as the length of the snare coil 140, its proximal attachment position relative to the distal aspect of the outer catheter 120, the number of incorporated rotations, the width of the coil wire, and the pitch of the loops will help determine the performance characteristics of the capturing mechanism, such as the maximal axial distance between the surface of the catheter and the uncoiled snare coil element 140, the axial motion with each rotation of the snare coil 140, and the potential engagement surface areas.

The design of the snare coil capturing device 100 can help overcome some of the design deficiencies and performance issues recognized in the presently available devices that are part of the prior art.

As previously mentioned, one object of the design incorporated in the snare coil retrieval device 100 is to provide a device that can more precisely manipulate and guide the engagement or retrieval wires to maximize nonrandom engagement with a foreign material. Most prior art devices have incorporated wires, struts or baskets that generally assume a pre-defined geometry once deployed without providing the ability to position them in the most optimal relationship to the object requiring retrieval (e.g., tissue specimen or foreign body material, etc.). Those devices that provide more precision however usually incorporate only single snare loops and therefore the efficiency in securing a foreign material is compromised by the reduced contact surface area of engagement.

Simpler designs, such as the Amplatz device and En Snare device, allow the orientation of the loops to be adjusted by rotating the control or connecting wire. It can be difficult to translate rotations of the wire into precise maneuvering of the snare loops to achieve a particular orientation relative to a foreign material. Moreover, since the snare loops are connected to a wire, their orientation may not be firmly fixed since the wire can accept a certain degree of torsional displacement or rotation.

However, the present invention overcomes these deficiencies and provides a structure in which, as the snare coil element 140 is continuously wound around the catheter each of the loops is confined in a controllable orientation relative to the catheter itself. Also, the orientation of the snare coil loop(s) 140 can be more easily directed by positioning the catheter itself and is not dependent on less reliable transmission of a wire rotation into a snare or loop orientation. Also, depending on the length and number of loops incorporated into the snare coil element 140, rotations of the inner tube or wire 130 can be translated into small precise changes in the diameters of the snare coil loops, thereby resulting in more precise engagement.

The present snare coil design 140 can also increase the surface contact area between the retrieval device 100 and the foreign body, thereby more securely engaging the material for removal.

As noted above, multiple wire basket or mesh designs increase the surface area of engagement only if the foreign material engages these in multiple niches or gaps or actually lodges within the basket structure itself. Also, as noted above since these capturing elements are hard to precisely guide, the chance of such an event may be random and therefore may be unlikely.

The snare coil retrieval device 100 is designed to secure foreign material against the outer wall of the outer catheter 120, which potentially provides a larger contact surface area than that seen in conventional single loop or multi-wire mesh designs. Moreover, the snare coil design of the device 100 in some sense can be thought of as a multi-looped capturing mechanism as each 180 degree turn of the snare coil 140 is equivalent to a snare loop. Although the snare coil design 140 does not provide for multiple individuals snare loops, there is a continuous elongated loop wound around the outer catheter 120 that potentially provides for a greater engagement surface when securing a foreign material against the outer surface of the catheter. Moreover, being able to substantially unwind the snare coil 140 allows for a significant gap to be opened between the surface area of the outer cannula 120 and the coil 140 itself, thereby improving the efficiency of engagement.

Figure 2:
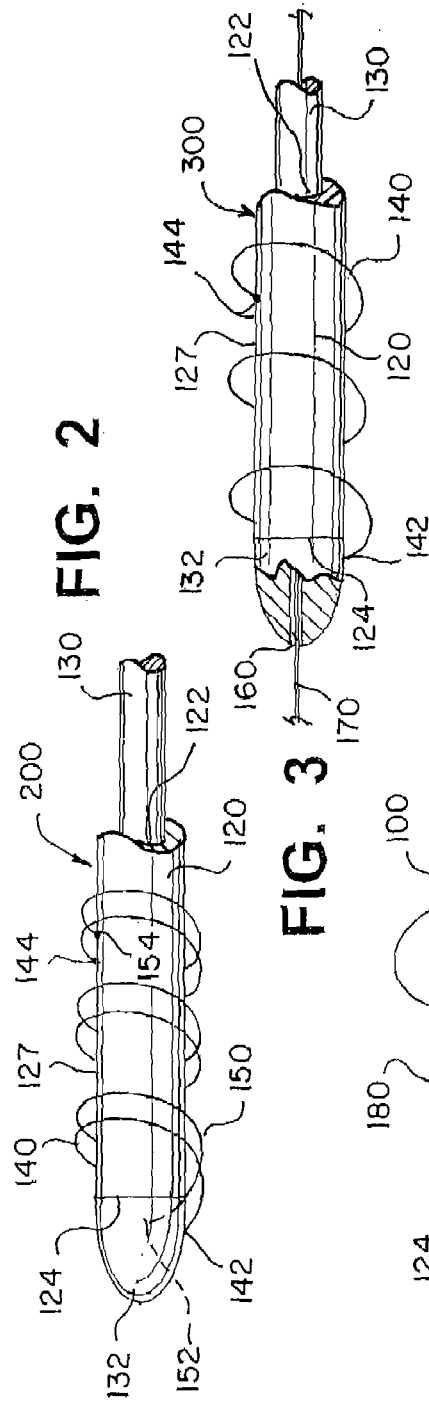
FIG. 2 is a side elevation view, in cross-section, of a specimen retrieval device according to a second embodiment.

Now referring to FIG. 2, in which a snare coil retrieval device 200 according to another embodiment is shown. The selection and applicability of the proper retrieval device will depend upon the requirements of the clinical situation.

In contrast to the device 100 of FIG. 1 which is a single wire system, the device 200 of FIG. 2 incorporates two or more wires or strands 140, 150. As previously mentioned, the snare coil 140 includes distal end 142 that is attached to the head 132 and the opposite proximal end 144 is connected to the outer surface 127 of the outer cannula 120. The proximal end 144 of the snare coil 140 is not attached at the most distal region of the outer cannula 120 but instead, the proximal end 144 is connected to the outer cannula 120 at a location that is spaced from the distal end 124 of the outer cannula 120. In contrast, the distal end 142 of the snare coil 120 is attached to the distal rotating end 132 of the inner element 130 (inner tube catheter). The remaining portion of the snare coil 140 surrounds the outer cannula 120.

Similar to the snare coil 140, the snare coil 150 has a distal end 152 that is also attached to the head 132 using any number of different techniques and an opposite proximal end 154 that is connected to the outer surface 127 of the outer cannula 120. The proximal end 154 of the snare coil 150 is not attached at the most distal region of the outer cannula 120 but instead, the proximal end 154 is connected to the outer cannula 120 at a location that is spaced from the distal end 124 of the outer cannula 120. In contrast, the distal end 152 of the snare coil 150 is attached to the distal rotating end 132 of the inner element 130 (inner tube catheter). The remaining portion of the snare coil 150 surrounds the outer cannula 120.

The snare coils 140, 150 are disposed in an interleaved relationship (arranged in an alternating fashion) in that the loops of the snare coil 140 are disposed next to the loops of the snare coil 150. In the illustrated embodiment, the proximal end 144 of the snare coil 140 is located closer to the proximal end of the outer cannula 120 compared to the proximal end 154 of the snare coil 150. However, the opposite arrangement can equally be true. While the ends 142, 152 of the snare coils 140, 150, respectively, are being shown as being attached to the head 132 of the inner tube 130 within one region of the head 132, it will be understood that the spacing between the ends 142, 152 can be greater and the ends 142, 152 can be attached in different locations. Similarly, the ends 144, 154 of the snare coils 140, 150, respectively, do not have to be attached to the outer surface of the cannula 120 in the same area of the outer surface.

Moreover, there are multiple variables that can be introduced to potentially increase the capturing ability of the retrieval device system. Although FIG. 2 shows two relatively independent coils 140, 150, multiple coils could be connected with interdigitating connector elements to provide a more meshlike system.

In another embodiment the coil loops of the snare coil can be made wider using a snare coil that is not composed of a single wire but instead, the snare coil can be formed of a strip of metal or alternatively composed of multiple wires woven together in a type of strip of mesh.

Figure 3:
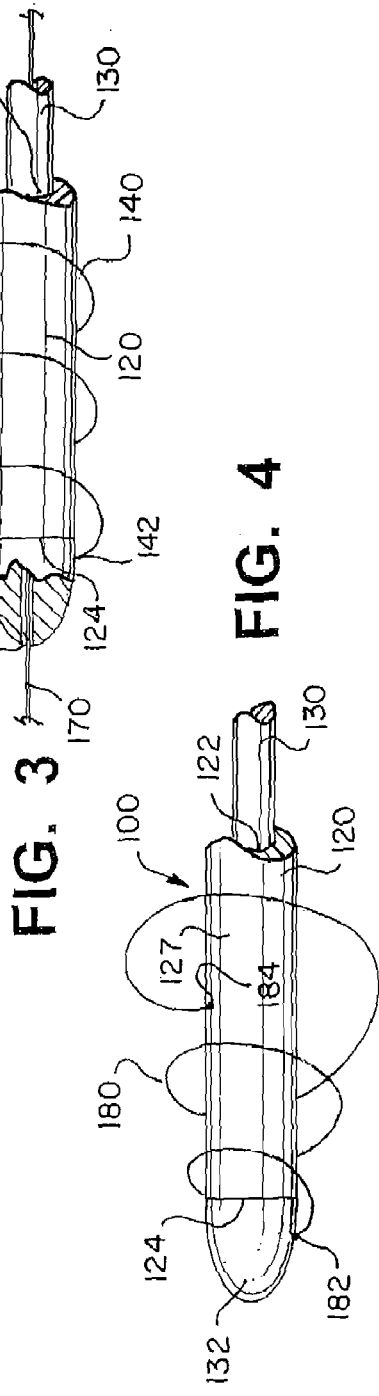
FIG. 3 is a side elevation view, in cross-section, of a specimen retrieval device according to a third embodiment.

Now referring to FIG. 3 in which a retrieval device 300 according to another embodiment is shown. The device 300 is very similar to the device 100 of FIG. 1; however and according to this embodiment, the inner member 130 includes a guide wire channel 160 for receiving a guide wire 170. The guide wire channel 160 is a longitudinally extending channel that extends the length of the inner member 130. More specifically, the guide wire channel 160 is a bore that extends from the proximal end and to and through the head 132 of the inner member 130. Preferably, the channel 160 is centrally located within the inner member 130; however, it does not have to be.

The guide wire channel 160 is thus incorporated into an internal solid rotating element 130 or is defined by the inner lumen of the inner tube/catheter 130 to provide a channel for the wire 170. The guide wire 170 can traverse through the channel or lumen 160. The operator first places the wire 170 into the structure (e.g., human body) in which the foreign body (e.g., foreign material or tissue specimen, etc.) is located, positioning it adjacent to the material. The snare coil retrieval device 300 can then be guided to the region of the foreign body material (or tissue specimen) using the guide wire 170 by advancing the device 300 along the wire 170 through the channel 160 to its appropriate position.

Figure 4:
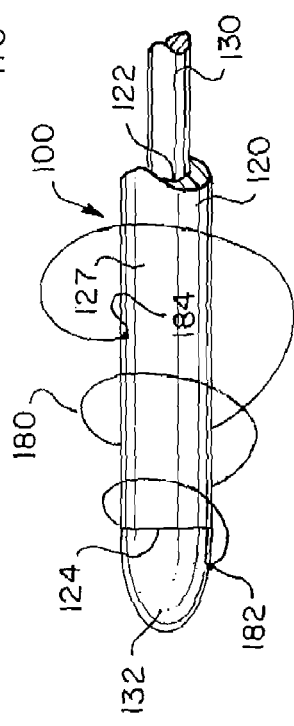
FIG. 4 is a side elevation view, in cross-section, of a specimen retrieval device according to a fourth embodiment.

The snare coil can also be made of a material that has memory, such as Nitinol, in order that there is a defined geometry to the opened coil. As seen in FIGS. 5a-5g, a device 301 can include a snare coil 180 that has a coil diameter that is smaller at a more distal aspect 182 of the snare coil 180 and is greater at a more proximal aspect 184 when the coil 180 is opened and deployed. The device 301 is similar to the devices shown in FIGS. 3 and 4 and therefore like elements are numbered alike. In particular, the inner element 130 includes the guide channel 160 fore receiving the guide wire 170 as shown in FIG. 5c and the coil 180 (FIG. 4) is used in the device 301.

Figure 5A:
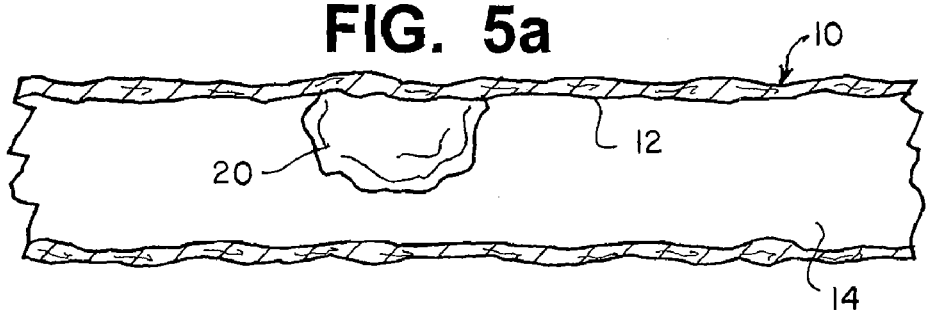
FIGS. 5a-5g are schematic cross-sectional views showing the progressive steps of the insertion of the device of FIG. 5 into a lumen structure for retrieval of a specimen.
Figure 5B:
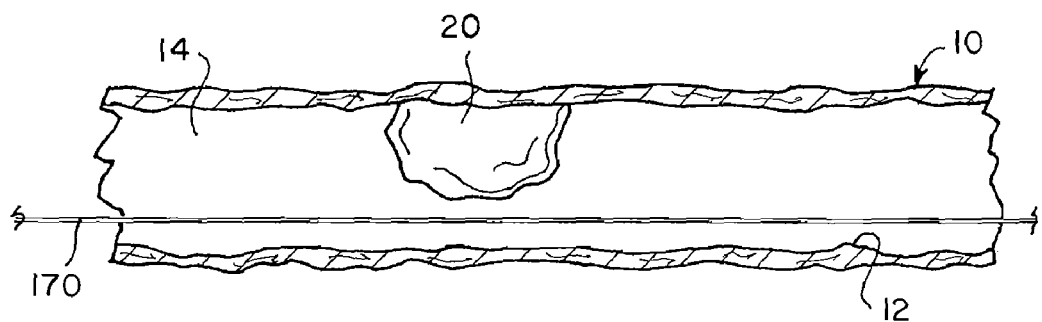
Figure 5C:
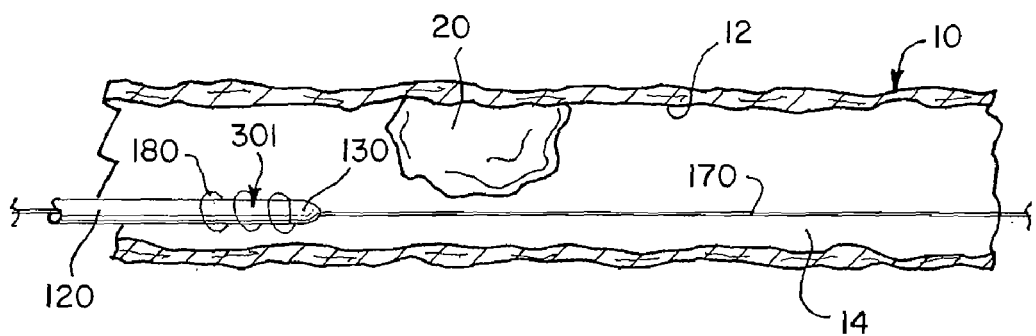
Figure 5D:
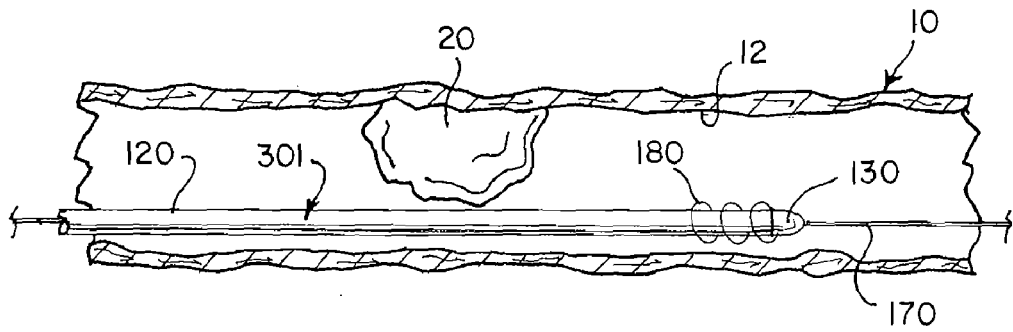
Figure 5E:
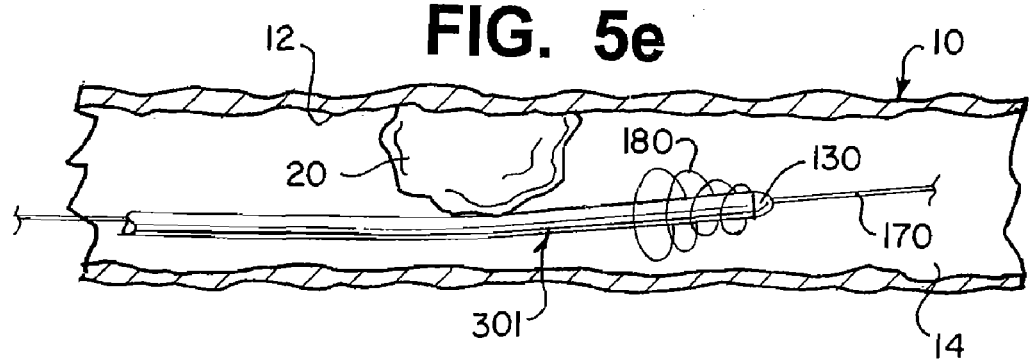
Figure 5F:
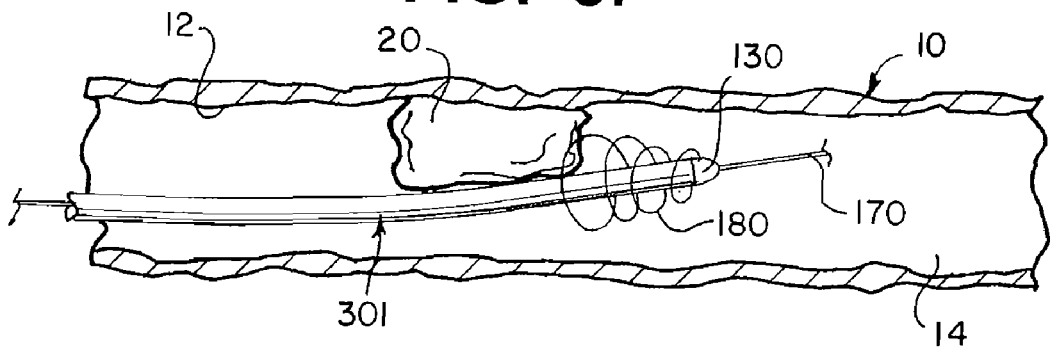
Figure 5G:
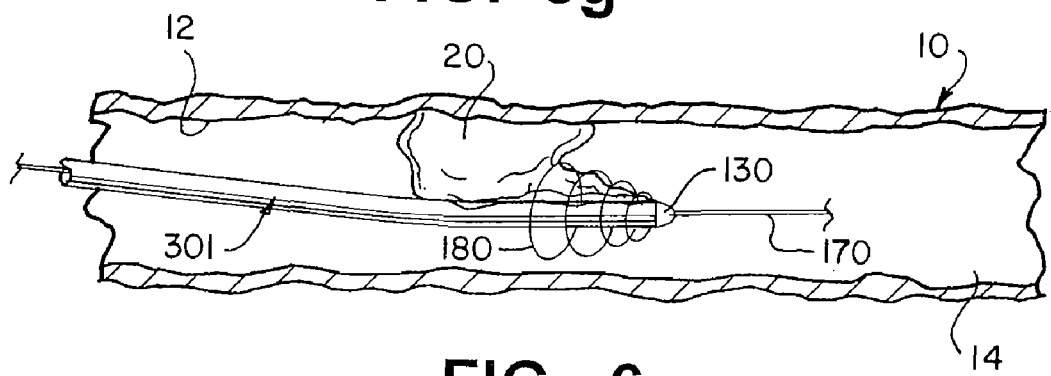

FIG. 5a illustrates a lumen-like structure 10, such as a duct or vascular channel (e.g., a blood vessel). The lumen-like structure 10 includes an inner wall 12 that defines a hollow interior 14 (a lumen or bore). Within the lumen 14, an object or foreign body 20, such as a thrombus within a blood vessel, is located and typically is attached along the inner surface of the outer wall 12. The foreign body 20 can represent a clot in a blood vessel 10 or it can be a stone in a duct 10. FIG. 5b shows the guide wire 170 being inserted into the lumen 14 and guided so that the wire 170 is disposed adjacent the foreign body 20. In FIG. 5c, the retrieval device 301 is inserted into the lumen 14 by inserting the wire 170 into the channel 160 formed through the inner member 130. As previously mentioned, this permits the device 301 to be guided along the wire 170 towards the area where the foreign body 20 is located inside the structure 10. In FIG. 5d, the device 301 is guided past the foreign body 20 so that the snare coil 180 is disposed beyond the foreign body 20 but the snare coil 180 is not yet activated.

This type of configuration would be particularly appropriate if the tip of the snare coil capturing mechanism 180 was placed distal to the object 20 in a vascular or other tissue space 10 (as shown in FIG. 5d). Once the snare coil 180 is opened or deployed (FIG. 5e), the device 301 and in particular, the snare coil 180 can be withdrawn backward onto the foreign body 20 (FIG. 5f) which can be more easily engaged as the more proximal loops 184 of the snare coil 180 have a greater diameter and thus, permit the object 20 to be more easily received into the snare coil 180. Once the snare coil 180 engages the object 20, the snare coil 180 can be closed (FIG. 5g) and the entire system (device 301) withdrawn. This type of system where the more proximal portion 184 of the snare coil 180 has a greater diameter than the distal portion 182 would serve more as a basket type of configuration and might find applicability in capturing "wider" substances, such as stones or irregular thrombi within a vascular channel as shown in FIGS. 5a-5g. In addition, the construction of the snare coil 180 permits a greater amount of the object 20 to be grasped and thereby retrieved and withdrawn from the lumen structure 10.

Figure 6:
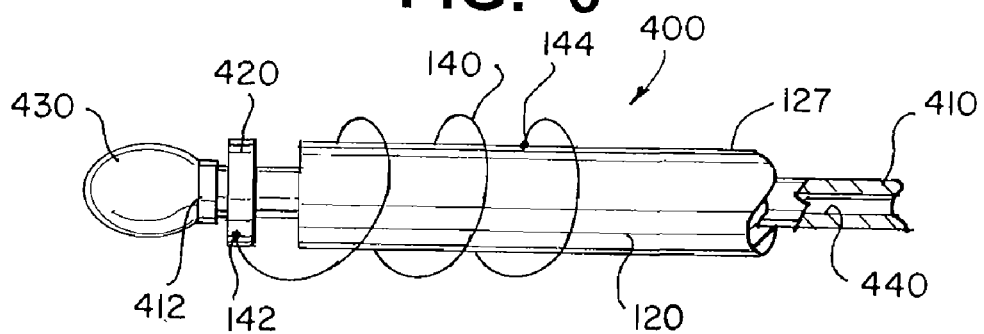
FIG. 6 is a side elevation view, in cross-section, of a specimen retrieval device according to a fifth embodiment.

Now referring to FIG. 6 in which another embodiment is shown and in particular, a retrieval device 400 is illustrated. The retrieval device 400 is similar to previous embodiments in that the device 400 includes the outer cannula 120 that includes an inner lumen or bore that extends therethrough from the proximal end to the distal end of the outer cannula 120.

The device 400 includes a rotatable inner member 410 that is received within the bore (channel) formed in the outer cannula 120. The inner member 410 can thus extend longitudinally within the bore formed through the outer cannula 120. The inner member 410 can therefore be in the form of a rotatable innertube or internal catheter that has a proximal end and an opposing distal end 412. Near or at the distal end 412, a connecting member or element 420 is provided for attachment to the snare coil element 140. In the illustrated embodiment, the connecting member 420 is an annular member (flange-like member) that extends around the inner member 410 and defines a surface to which a distal aspect (end) of the snare coil element 140 is attached. The shape and size of the connecting member 420 are not critical so long as the distal aspect of the snare coil element 140 can be attached thereto; however, the connecting member 420 has dimensions that are greater than the dimensions of the bore formed in the outer cannula 120 and therefore, the connecting member 420 acts as a stop since the connecting member 420 cannot be received into the bore of the outer cannula 120. The proximal aspect (end) of the snare coil element 140 is attached to the outer surface 127 of the outer cannula 120 as in the other embodiments.

The inner member 410 includes an expandable member 430 that is located distally beyond the connecting member 420 and therefore, the expandable member 430 represents the distalmost section of the inner member 410. The expandable member 430 can be controllably inflated to increase its size and can be controllably deflated to decrease its size. In one embodiment, the expandable member 430 is in the form of a balloon that can be expanded or deflated and is attached to the end (e.g., a stem structure) of the inner member 410. In order to inflate and deflate the expandable member 430, the inner member 410 includes an internal channel or passageway 440 that delivers air or another gas or liquid to the expandable member 430 for inflating or deflating the member 430. A gas source can be fluidly connected to channel 440 and operation of the gas source permits a gas to be delivered or removed from the expandable member 430 for inflating or deflating the expandable member 430, respectively.

If the snare coil device 400 is placed beyond a thrombus or embolus and it is the intent of the operator to remove the material without any of it or a portion of it is moving "forward" or distally once the system is placed beyond the thrombus, the expandable member (balloon) 430 can be inflated. Subsequently, the snare coil 140 can be wound down onto the foreign material or thrombus to capture it. If any material is dislodged during the capturing mechanism, the expandable member 430 impedes the material from moving forward if the expandable member 430 has been inflated. It will be understood that the expandable member 430 can remain deflated if it is not needed for a given application.

Figure 7:
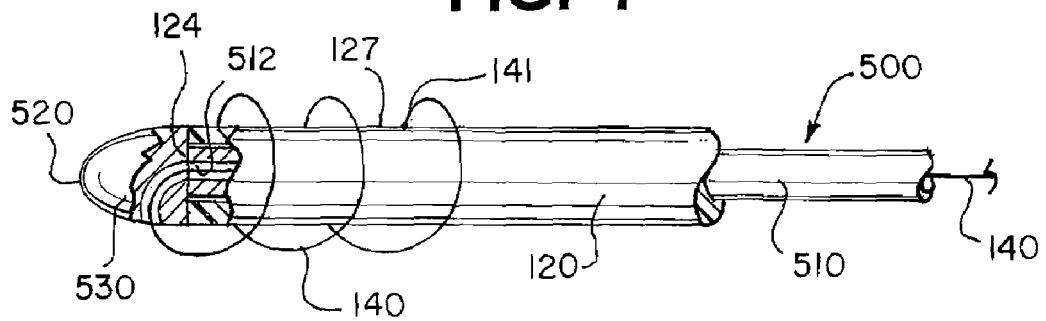
FIG. 7 is a side elevation view, in cross-section, of a specimen retrieval device according to a sixth embodiment.

Now referring to FIG. 7 in which another embodiment is shown and in particular, a retrieval device 500 is illustrated. The device 500 is very similar to the device 100; however, this embodiment allows for the ability to increase the length of the snare coil wire 140 to potentially increase the axial diameter of the snare coil element 140, if required, to encompass the wire or wires around a more irregular or larger foreign body material.

As shown in FIG. 7 and in contrast to the other designs, the distal portion of the snare coil wire 140 is not fixed at the distal tip (end) of an inner rotatable member 510 that is similar to the inner member 130. In this embodiment, the inner rotatable member 510 has a channel 512 that is formed therethrough from the proximal end of the inner member 510 to the distal end of the inner member 510. The channel 512 receives the snare coil wire 140 which exits at a distal region 520, such as a head 530, of the inner member 510 and forms the snare coil element (loops) 140. One distal free end 141 of the snare coil wire 140 that defines the snare coil loops is attached to the outer surface 127 of the outer cannula 120.

If an additional wire 140 length is required to capture a more complex structure (more complex tissue sample), more wire 140 can be "fed" out the tip to help encompass or grab the foreign body 20 (FIG. 5a), thereby increasing the diameter of the snare coil loops. Subsequently, the wire length can be decreased by pulling back the wire 140 into the inner tube system 130. Simultaneously or subsequently, the inner tube system 130 can be rotated to wind down the snare coil 140 and help capture the foreign body 20.

Depending upon the number of turns incorporated in the snare coil element 140, it may take multiple revolutions of the inner tube 130 to wind the snare coil 140 down adequately to grab a foreign material 20. The operator should not be encumbered with rotating the inner tube 130 while they are concentrating on the position of the tip/snare coil element 140 and engaging the foreign material 20.

Figure 8:
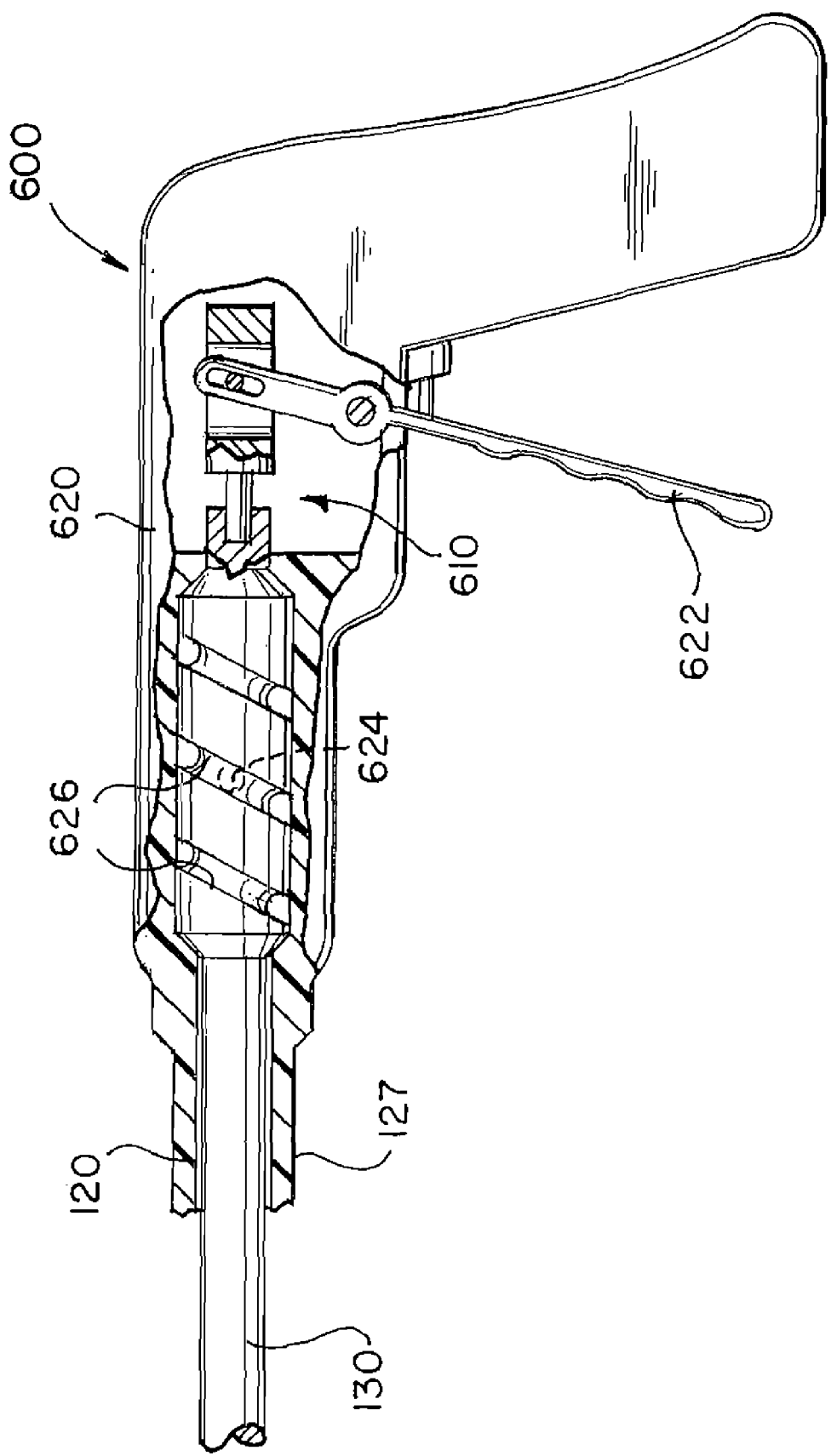
FIG. 8 is a side elevation view, in cross-section, of a handle portion of a specimen retrieval device according to a seventh embodiment.

Other mechanisms can be defined to facilitate the process of rotating the inner tube or element 130. The rotatable inner element 130 can be connected to a hand-held device that converts a grasping motion into rotation using a pin and groove mechanism as shown in FIG. 8. In particular, FIG. 8 shows a retrieval device 600 that includes a simple pin and groove mechanism 610 that is incorporated into a handle housing 620 and is constructed so that when an operator squeezes a handle 622, this action is converted into a rotation of inner tube or wire 130 relative to the outer cannula 120. For example, the handle 622 can include a pin member (protrusion) 624 and the inner tube 130 includes a groove 626 that is formed about the outer surface of the inner tube 130. The groove 626 has a helical shape or any other type of shape that will impart rotation to the inner tube 130. The pin 625 couples the proximal end of the inner tube 130 to the handle in such a way that the inner tube 130 can rotate relative to the handle 622.

As the handle 622 is moved (e.g., axial movement), the pin 624 is advanced within the groove 626 and the helical shape of the groove 626 causes and imparts rotation to the inner tube 130.

It will also be understood that the opposite arrangement can be true in the pin element can be formed as part of the inner tube 130 and the groove can be part of a handle component. The result is the same in the movement of the handle is translated into rotational movement of the inner tube 130.

Depending upon the mechanical relationship between the pin and groove mechanism, a small movement of the handle 622 can result in multiple revolutions of the internal element (inner tube 130), and a relatively finally controlled quick winding down of the snare coil 140 onto a foreign body. The pin and groove system also could be mechanized using a motor system, and the motor could be controlled with a foot pedal allowing the operator to concentrate on the position of the snare coil tip.

In yet another aspect of the present invention, the retrieval device can have radio opaque material placed on the snare coil 140 so that it could be easily seen during the radiographic procedure and the opening and coiling of the snare coil 140 could be visualized and controlled precisely which is a proposed advantage of the new system.

There are a number of embodiments that can be designed to increase the rigidity of the distal portion of the micro catheter (outer cannula 120) in order to increase the capturing force applied to the foreign body between the distal aspect of the catheter 120 and the snare coil 140. In one such design, metal braiding is placed within the wall of the distal centimeter or two of the micro catheter (outer cannula 120). Alternatively, a thin metal coating could be applied to the outer surface of the catheter (outer cannula 120) or even a thin metal sleeve could be placed in that position.

Figure 9:
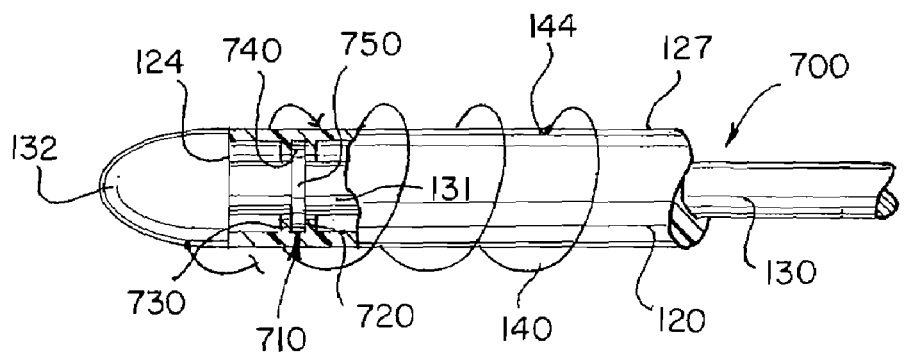
FIG. 9 is a side elevation view, in cross-section, of a specimen retrieval device according to an eighth embodiment.

In order that the inner tube or wire 130 does not move forward, a ring system can be employed either at the proximal portion of the micro catheter (outer cannula 120) or even at the distal portion adjacent to the tip of the rotating inner tube 130. For example, FIG. 9 shows another embodiment of the present invention in which a retrieval device 700 is shown and is similar to the devices of the other embodiments. The retrieval device 700 includes a locating member or feature 710 designed to limit or prevent longitudinal movement of the inner tube 130 and snare coil 140 relative to the outer cannula 120.

For example, the locating member 710 can be in the form of a first flange member (first annular flange) 720 and a second flange member (second annular flange) 730 that is spaced from the first flange member 720. The first and second flange members 720, 730 are disposed within the inner lumen (bore) of the outer cannula 120 and are attached or integrally formed as part of the inner surface of the outer cannula 120. In FIG. 9, the flange member 720, 730 thus appear as ring structures that are spaced from one another as to define an annular space 740 therebetween.

It will be appreciated that the inner diameter of the flange member 720 and the inner diameter of the flange member 730 is greater than an outer diameter of a body portion 131 of the inner tube 130. In other words, the body portion 131 of the inner tube 130 is able to be received within the openings defined by the flange members 720, 730 so as to allow the inner tube 130 to enter the bore of the outer cannula 120 and extend a length therein.

The remaining components of the device 700 are the same as the device 100 in that the inner tube 130 has an enlarged head 132 and a snare coil 140 is attached at one end to the head 132 and at the other end to the outer surface 127 of the outer cannula 120. However, the inner tube 130 includes an engagement member 750 that is designed to be received within the space 740 formed between the flange members 720, 730. The engagement member 750 is constructed so that when it is received within the space 740, the inner tube 130 can still freely rotate relative to the outer cannula 120; however, the inner tube 130 only has a small degree of longitudinal movement with respect to the outer cannula 120.

The engagement member 750 can be in the form of one or more protrusions or flanges that extend radially outward from an outer surface of the inner tube 130. In the illustrated embodiment, the engagement member 750 is in the form of an annular flange that extends radially outward from the outer surface of the inner tube 130. The engagement member 750 can be integrally formed as part of the inner tube 130 or it can be attached thereto.

It will also be appreciated that instead of placing the locating feature 710 at the distal end of the outer cannula 120, the locating feature can instead be located at the proximal end of the outer cannula 120 or in another embodiment, the locating feature 710 can be formed at both the proximal and distal ends of the outer cannula 120 to minimize any longitudinal displacement of the inner tube 130 or the snare coil 140.

Figure 10:
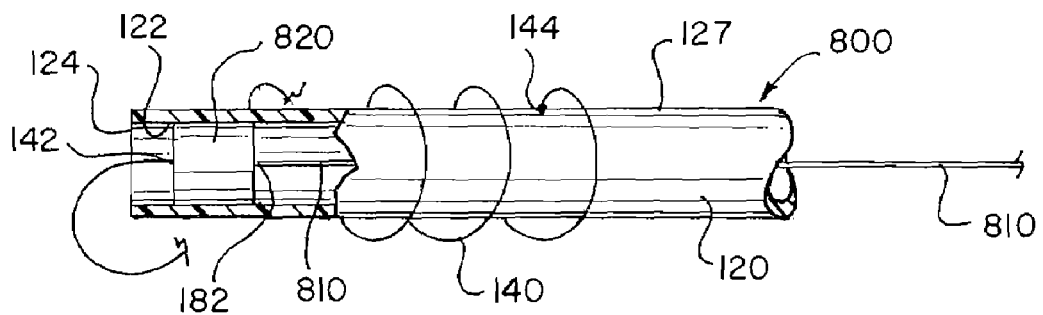
FIG. 10 is a side-elevation view, in cross-section, of a specimen retrieval device according to an eighth embodiment.

Now referring to FIG. 10 in which a specimen retrieval device 800 according to another embodiment is illustrated. The device 800 shares some of the common elements found in previous embodiments and therefore, like components are numbered alike. For example, the device 800 includes an outer cannula 120 that is open at both ends including the distal end 124. As with the other embodiments, the device 800 is of a snare coil design; however, in contrast to having a rotatable inner member in the form of a cannula, the device 800 includes an inner rotatable member 810 in the form of a wire. The wire 810 is disposed within the interior 122 of the outer cannula 120 and extends the length thereof and is accessible at the proximal end of the outer cannula 120 to permit the operator to be able to grasp the wire 810 and rotate it for actuation of the snare.

At a distal end of the wire 810, a locating and support member 820 is provided and is generally in the form of a structure (e.g., a cylindrically shaped member, a block or other shaped member) that is dimensioned to be received and to travel within the bore 122. The support member 820 is wider than the wire and is constructed to maintain the distal end of the snare coil 140 in a central location within the outer cannula 120. A distal end 182 of the wire 180 is attached to one face of the support member 820, while the proximal end of the wire 810 is accessible to the operator for rotating the wire 810.

The snare coil 140 has a distal end 142 that is attached to another face of the support member 820 and a proximal end 144 of the snare coil 140 is attached to the outer surface of the outer cannula 120. The support member 820 minimizes the possibility that the distal end 142 of the snare coil 140 displaces towards the inner surface of the cannula 120 during wire rotation or during longitudinal displacement of the wire 810. Also, the support member 820 is not fixed in the longitudinal position so that it can be moved proximally or distally within the lumen 122 of the outer cannula 120, thereby changing the diameter of the loops of the snare coil 140.

The embodiment of FIG. 10 has a distalmost loop that connects the support member 820 that connects the snare coil 140. Maintaining the geometry of the distalmost loop will be important in maintaining orientation/geometry of the snare coil 140 relative to the outer surface of the outer cannula 120. Therefore, the distalmost loop may need to be constructed with a slightly more rigid material or material that has memory.

The device 800 operates in a manner that is similar to how the device 100 operates in that rotation of the wire 810 causes the closing of the snare coil 140 when it is rotated in a first direction and causes the opening of the snare coil 140 when the wire 810 is rotated in the opposite second direction.

The device 800 offers a simple yet effective design that allowed the wire 810 to move longitudinally within the outer cannula 120 as in the embodiment shown in FIG. 7 and this permits the operator to either feed an additional length of wire 810 into the outer cannula 120 to cause an expansion of the coils of the snare coil 140 and conversely, the wire 810 can be pulled backward to cause a reduction in the size of the loops of the snare coil 140.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. A retrieval device for collecting a specimen comprising:
an outer cannula member having an inner lumen;
an inner member received within the inner lumen such that the inner member can rotate relative to the outer cannula, the inner member having a solid distal end and a guide channel formed in the inner member at a location spaced from the distal end, the guide channel being open at a distal end along a side of the inner member, the guide channel being open at an opposite proximal end, the side of the inner member being continuous with an outer surface of the outer cannula when the inner member is in a first position and a head of the inner member is disposed adjacent a distal end of the outer cannula member; and
a first snare coil having a first distal end and an opposing second proximal end, the first end of the snare coil being fixedly attached to an outer surface of the outer cannula, the snare coil having a portion that is looped about the outer cannula from the first end of the snare coil to the opening of the guide channel spaced from the distal end of the inner member where the snare coil enters the guide channel and extends therethrough such that the second end of the snare coil passes through the opening of the guide channel spaced from the distal end of the inner member to allow a length of the snare coil to be varied by an operator for increasing a diameter of the snare coil loops, the snare coil being actuated by rotating the inner member relative to the outer cannula so as to either open or close the snare coil for collecting the specimen.

2. The device according to claim 1, wherein the snare coil is formed of a material that has memory so that the snare coil has a predetermined, defined geometry as it opens.

3. The device according to claim 2, wherein the predetermined, defined geometry is one in which a coil diameter is greater in a proximal region of the snare coil compared to a distal region of the snare coil as measured when the snare coil is in an open position.

4. The device of claim 1, wherein the specimen comprises a pathologic material selected from the group consisting of thrombi, emboli and stone excrescenses.

5. The device of claim 1, wherein the inner member moves longitudinally within the inner lumen.

6. The device of claim 1, wherein the distal end of the inner cannula comprises an enlarged head with the distal opening of the guide channel being formed therethrough.

7. The device of claim 6, wherein the opening formed in the head of the inner member is axially offset from a linear main portion of the guide channel that is surrounded by the outer cannula.

8. The device of claim 6, wherein the opening is offset and spaced from a distalmost end of the head and a portion of the guide channel formed in the head is curved so as to deliver the snare coil to the main portion of the guide channel.

9. A method for capturing and retrieving a specimen from a site comprising the steps of:
    positioning a retrieval device proximate the specimen, the retrieval device including an outer cannula member having an inner lumen and an inner member received within the inner lumen and being rotatable relative to the outer cannula, the inner member having a solid distal end and a guide channel formed in the inner member at a location spaced from the distal end, the guide channel being open at an opposite proximal end, the device having a first snare coil having a first distal end and an opposing second proximal end, the first end of the snare coil being fixedly attached to an outer surface of the outer cannula, the snare having a portion that is looped about the outer cannula from the first end of the snare coil to the opening of the guide channel spaced from the distal end of the inner member where the snare coil enters the guide channel and extends therethrough such that the second end of the snare is accessible at a proximal end of the inner member;
    positioning the snare coil proximate the specimen and opening the snare coil by moving one of the inner member and snare so as to cause diameters of loops of the snare about the outer cannula to increase;
    capturing the specimen within at least one loop of the opened snare coil; and
    longitudinally moving the snare within the inner member in a direction toward the proximal end of the inner member to close the snare coil with the specimen being captured therein and then withdrawing the retrieval device from the site.

10. The method of claim 9, wherein the snare coil is constructed so that as the snare coil is opened, a proximalmost loop of the snare coil has a greater diameter compared to the other snare coil loops and the step of capturing the specimen comprises the step of opening up the proximalmost loop so that the specimen is captured therein.

11. A retrieval device for collecting a specimen comprising:
    an outer cannula member having an inner lumen;
    an elongated wire disposed within the inner lumen such that the inner member can rotate relative to the outer cannula, the wire having a distal end and a proximal end that is accessible at a proximal end of the outer cannula;
    a support member disposed within the inner lumen at or proximate a distal end thereof, the support member being rotatable relative to the outer cannula and movable in a longitudinal direction within the inner lumen, the support member having a first exterior surface that is attached to the distal end of the wire and an opposite second exterior surface; and
    a snare coil having a first end and an opposing second end, the first end of the snare coil being attached to an outer surface of the outer cannula and the second end of the snare coil being fixedly attached to the second surface of the support member, wherein the support member is positionable in an actuated position where the support member is entirely disposed within the inner lumen and the snare coil is actuated and wound down around the outer cannula for collecting the specimen, wherein in the actuated position, the support member is located further away from the distal end of the outer cannula than when the support member is in a position where the snare is open.

12. The device of claim 11, wherein the support member comprises a block that is movable longitudinally within the inner lumen.

13. The device of claim 11, wherein at least a distalmost loop of the snare is formed of one of a rigid material and a material that has memory.

14. The device of claim 11, wherein the wire comprises a rigid wire that does not freely bend.

15. The device of claim 11, wherein the specimen comprises a pathologic material selected from the group consisting of thrombi, emboli and stone excrescenses.

16. The device of claim 1, wherein the inner member includes an inner tube section that is coupled to the head, the head having a width that is greater than a width of the inner tube section.

17. The device of claim 16, wherein the guide channel comprises a curved channel formed in the head that opens along the side of the head.

18. A retrieval device for collecting a specimen comprising:
    an outer cannula member having an inner lumen, the outer cannula having a distal end;
    an inner member received within the inner lumen such that the inner member can rotate relative to the outer cannula, the inner member having a central bore formed therein; and
    a first snare coil disposed within the central bore and having a first distal end and an opposing second proximal end, the first end of the snare coil being fixedly attached to an outer surface of the outer cannula by passing through an opening formed in the inner member at a location beyond the distal end of the outer cannula, the snare coil having a portion that is looped about the outer cannula from the first end of the snare coil to the opening in the inner member where the snare coil enters the inner member and passes into the central bore and extends therethrough such that the second end of the snare coil is disposed at a proximal end of the inner member, the snare being movable longitudinally within the central bore to cause the snare to assume an actuated position when the second end of the snare is moved to a position that extends beyond the proximal end of the inner member, thereby allowing a length of the snare coil to be varied by an operator for increasing and decreasing a diameter of the snare coil loops so as to either open or close the snare coil for collecting the specimen.

* * * * *